Nishizawa et al.

[11] 4,269,188
[45] May 26, 1981

[54] DISPOSABLE DIAPER

[75] Inventors: Kazunori Nishizawa, Funabashi; Toshihiro Shirose, Soka; Osamu Itoh, Funabashi, all of Japan

[73] Assignee: Kao Soap Co., Ltd., Tokyo, Japan

[21] Appl. No.: 59,500

[22] Filed: Jul. 23, 1979

[30] Foreign Application Priority Data

Jul. 28, 1978 [JP] Japan .................................. 53/92196

[51] Int. Cl.³ ............................................ A41B 13/02
[52] U.S. Cl. ....................................................... 128/287
[58] Field of Search .................... 128/284, 287, 290 R

[56] References Cited

U.S. PATENT DOCUMENTS

| 3,670,731 | 6/1972 | Harmon | 128/287 |
| 4,055,180 | 10/1977 | Karami | 128/287 |
| 4,102,340 | 7/1978 | Mesek et al. | 128/287 |

FOREIGN PATENT DOCUMENTS 2636899  3/1977  Fed. Rep. of Germany ........... 128/287

Primary Examiner—Kyle L. Howell
Assistant Examiner—C. F. Rosenbaum
Attorney, Agent, or Firm—Blanchard, Flynn, Thiel, Boutell & Tanis

[57] ABSTRACT

A disposable diaper comprises an absorbing material comprising a sheet containing water-absorbing polymer powder and two papers to fix said powder between them, a great number of slits being formed on said sheet, and fluff pulp layers sandwiching said sheet, among said two papers the paper which is close to the surface of the diaper where to contact with the skin being a high wet strength paper, the paper which is close to the back face of the diaper being a low wet strength paper.

4 Claims, 3 Drawing Figures

DISPOSABLE DIAPER

The present invention relates to an improved disposable diaper.

Water-absorbing paper or fluff pulp has heretofore been used as an absorbing material of a disposable diaper. Recently, utilization of a water-absorbing polymer as the absorbing material of a disposable diaper has been tried. Application of a water-absorbing polymer to a disposable diaper is ordinarily performed according to a method in which the powdery water-absorbing polymer is fixed between two papers. However, when the water-absorbing polymer fixed sheet assembly (hereinafter referred to as "water-absorbing sheet") absorbs water, the water-absorbing polymer is swollen with water and passage of urine through the water-absorbing sheet tends to become gradually slower. As means for overcoming this defect, we previously developed a disposable diaper comprising a water-absorbing sheet on which a great number of slits are formed. In such a disposable diaper, the above-mentioned defect is eliminated, but because of the improved urine passage, also the speed of urine returning to the upper layer from the lower layer of the fluff pulp through the slits is increased. In order for the water-absorbing polymer to exert the water-absorbing function most effectively, a sufficient time should be provided for the contact between urine and the water-absorbing polymer. Therefore, from the practical viewpoint, this disposable diaper is still insufficient.

Accordingly, we made researches with a view to eliminating this disadvantage, and as a result, it was found that in order to attain a practically satisfactory effect, it is important to impart a directive characteristic to the above-mentioned slits. More specifically, it is important to impart to the slits such a one-way characteristic that urine permeating from the surface of the diaper is allowed to pass through the slits on the water-absorbing sheet and permeate into the lower layer of the fluff pulp but it is scarcely returned to the upper layer of fluff pulp even under compression by the body weight of a baby. When such characteristic is provided, the water-absorbing polymer can exert the water-absorbing function most effectively because a sufficient contact time is ensured, and it is considered that since the return of urine to the surface portion is effectively inhibited, practically satisfactory results can be obtained.

The present invention has been completed based on the above-mentioned technical idea.

More specifically, in accordance with the present invention, there is provided a disposable diaper which comprises an absorbing material comprising a sheet including a water-absorbing polymer powder fixed between two papers, a great number of slits being formed on said sheet, and fluff pulp layers sandwiching said sheet, said disposable diaper being characterized in that in said two papers of the polymer-fixed sheet, the paper close to the surface of the diaper (disposed in the direction falling in contact with the skin) is a high wet strength paper and the paper close to the back face of the diaper is a low wet strength paper.

The water absorbing polymer to be used in the invention includes, for example, insolubilized hydrogel, as taught in U.S. Pat. Nos. 3,664,343, 3,783,872, 3,669,103, 3,670,731, and Japanese patent publication (unexamined) No. 35685/1976 corresponding to U.S. Ser. No. 492,897 filed July 29, 1974, now U.S. Pat. No. 3,901,236. Embodiments for it are polyethylene oxide, polyvinyl pyrrolidone, polyacrylic amide, partially hydrated polyacrylic amide, polyvinyl alcohol, maleic anhydride-vinyl ether copolymer, maleic anhydride-vinylpyrrolidone copolymer, polyacrylic acid, ethylene-maleic anhydride copolymer, polyvinyl ether, dextrane, agar, gelatin, hydroxypropyl cellulose, methyl cellulose, carboxymethyl cellulose, hydroxyethyl-carboxymethyl cellulose, hydroxyethyl cellulose, propyleneglycol alginate, sodium alginate, polyethylene imine, polyvinyl-alkylpyridinium halide, polyvinyl morpholinone, polymer and copolymer of vinylmorpholine, polymer and copolymer of vinylsulfonic acid and their ammonium or alkali metal salts, amide, alkali metal or ammonium salts derived from copolymer of maleic anhydride and vinylmethyl ether vinylpyrrolidone, vinylmorpholine or mono-olefinic hydrocarbon, acrolein polymer or copolymer denatured with alkali metal hydroxide or alkali metal bisulfate, copolymer of sulfur disulfide and allyl alcohol, allyl ether of glycerol, allyl ether of ethylene glycol or polyethylene glycol, polyvinyl-n-butylpyridinium bromide, polyproline, natural starch, denatured starch (U.S. Pat. No. 3,661,815 and U.S. Ser. No. 456,911 filed Mar. 3, 1974 now U.S. Pat. No. 3,935,099), casein, protein, polymethacrylic acid, polyvinyl sulfonic acid, polystyrene sulfonic acid, polyvinyl amine, ammonium polyacrylate, hydroxyalkyl acrylate, hydroxyalkyl methacrylate, hydroalkoxy acrylate, hydroalkoxy methacrylate, polyethylene oxide-added ester of acrylic acid or methacrylic acid, alkoxyacrylate, alkoxymethacrylate, alkoxyalkyl acrylate, alkoxyalkyl methacrylate, partially hydrated polyacrylic amide, poly-4-vinylpyridine quaternary ammonium salt, olefinic acid monoester polymer, olefinic acid diester polymer, acrylic amide, and difunctional polymeric substances such as di-acid, diester and diamide.

The high wet strength paper to be used in the invention includes those disclosed in Japanese patent publication (unexamined) No. 103545/1976 corresponding to U.S. Ser. No. 525,254 filed Nov. 19, 1974, now U.S. Pat. No. 3,952,745. For example, high wet strength tissue paper having the minimum wet strength of at least about 55 grams per one inch may be used.

The low wet strength paper may be normal paper not treated for the purpose of the high wet strength, for example, include crepe paper and tissue paper.

Figure 1:
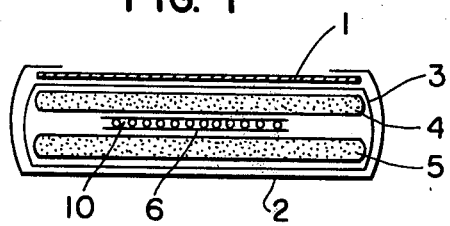
FIG. 1 is a sectional view illustrating one embodiment of the disposable diaper of the present invention.

In the drawings, 1 indicates a non-woven fabric, 2 indicates a liquid-impermeable sheet, 3 indicates tissue paper, 4 indicates an upper layer of fluff pulp, 5 indicates a lower layer of fluff pulp, 6 indicates a water-absorbing sheet, 7 indicates slits in the water-absorbing sheet, 8 indicates high wet strength paper, 9 indicates low wet strength paper, and 10 indicates water-absorbing polymer powder.

Figure 2:
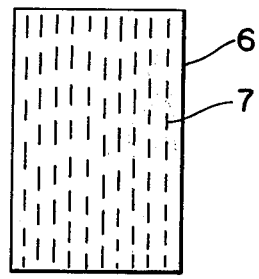
FIG. 2 is a plan view showing the appearance of the water-absorbing sheet.
Figure 3:
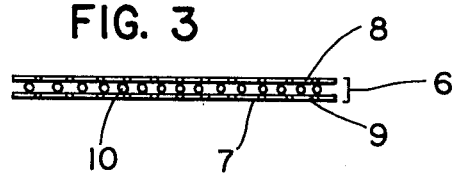
FIG. 3 is an enlarged view showing the section of the water-absorbing sheet.

The present invention will now be described in detail by reference to one embodiment illustrated in the accompanying drawing. As illustrated in FIG. 1, in the disposable diaper of the present invention, a water-absorbing sheet 6 including two papers 8 and 9, between which a water-absorbing polymer powder 10 is fixed, is interposed between two fluff pulp layers 4 and 5 formed to have an appropriate size, and this assembly is covered with a tissue paper 3, a liquid-impermeable sheet 2 and a non-woven fabric 1. The disposable diaper of the present invention is characterized in that a great number of slits 7 are formed in the papers 8 and 9 of the water-absorbing sheet 6 as shown in FIG. 2, and that as shown in FIG. 3, the paper 8 close to the surface of the diaper is a high wet strength paper and the paper 9 close to the back face is a low wet strength paper.

The present invention will now be described in detail by reference to the following Example.

EXAMPLE 26 g of fluff pulp was divided into two parts to form an upper layer and a lower layer. A water-absorbing polymer was fixed in an amount of 20 g/m$^2$ between two papers shown in Table 1 to form a water-absorbing sheet. A chemically bonded non-woven fabric composed of 80% of polyester fibers and 20% of rayon fibers, which had a base weight of 24 g/m$^2$, was used as the non-woven fabric. Thus, a diaper having a structure as shown in FIG. 1 was prepared. The properties of the so prepared diaper were examined to obtain results shown in Table 1.

TABLE 1

| Sample No. | Paper Structure of Water-Absorbing Sheet | | Time (sec) Required for Absorption of 60 cc of Synthetic Urine | Amount (g) of Returned Urine When 60 cc of Synthetic Urine Was Absorbed | Amount (g) of Returned Urine When 105 cc of Synthetic Urine Was Absorbed | Remarks |
| --- | --- | --- | --- | --- | --- | --- |
| | upper paper | lower paper | | | | |
| 1 | high wet strength paper A | low wet strength paper | 90 | 5.4 | 17.3 | present invention |
| 2 | high wet strength paper A | high wet strength paper A | 91 | 7.3 | 29.8 | comparison |
| 3 | low wet strength paper | low wet strength paper | 124 | 8.2 | 30.3 | comparison |
| 4 | high wet strength paper B | low wet strength paper | 89 | 5.1 | 16.8 | present invention |
| 5 | high wet strength paper C | low wet strength paper | 86 | 5.2 | 16.2 | present invention |
| 6 | low wet strength paper | high wet strength paper A | 120 | 6.9 | 31.4 | comparison |

Note
high wet strength paper A: containing 0.2% of Kymene 557H (manufactured by Dic Hercules Chemical Co.) and having a base weight of 30 g/m$^2$
high wet strength paper B: containing 20% of SWP (manufactured by Mitsui Gelapack Co.) and having a base weight of 20 g/m$^2$
high wet strength paper C: containing 25% of SWP (manufactured by Mitsui Gelapack Co.) and having a base weight of 20 g/m$^2$
low wet strength paper: having a base weight of 30 g/m$^2$ In Table 1, by the term "time required for absorption" is meant the time (expressed in terms of seconds) required for absorption of 60 cc of urine from a vessel placed on the surface of the diaper through a hole having a diameter of 1 cm, which was formed on the vessel. After 60 cc or 105 cc of urine had been absorbed in the above-mentioned manner, the diaper was allowed to stand still for 2 minutes and a load of 40 g/cm$^2$ was then applied in an area of 100 cm$^2$ around the absorption point, and the amount of urine that oozed out from the diaper was measured. This amount is indicated as the amount of returned urine in Table 1.

When sample 1 is compared with sample 6, it will readily be understood that the diaper of the present invention retains urine better.

As will be apparent from the foregoing illustration, in the disposable diaper of the present invention, by adoption of the above-mentioned specific structure, the urine absorbing speed is enhanced and the urine-absorbing efficiency of the water-absorbing polymer is improved.

The embodiments of the invention of which an exclusive property or privilege is claimed are as follows:

1. In a disposable diaper comprising a liquid-permeable top sheet, a liquid-impermeable bottom sheet, an upper layer of fluff pulp disposed between said top and bottom sheets and being located adjacent said top sheet, a lower layer of fluff pulp disposed between said top and bottom sheets and being located adjacent said bottom sheet, and a water-absorbing sheet disposed between said upper fluff pulp layer and said lower fluff pulp layer, said water-absorbing sheet being made of upper and lower plies having particles of water-absorbing polymer confined therebetween, said upper and lower plies being located adjacent said upper fluff pulp layer and said lower fluff pulp layer, respectively, said upper and lower plies both having a multitude of slits therethrough, the improvement which comprises: said lower ply is made of a low wet strength paper and said upper ply is made of a high wet strength paper so that urine can permeate relatively freely from said upper fluff pulp layer through the slits into said lower fluff pulp layer and permeation of urine in a direction from said lower fluff pulp layer toward said upper fluff pulp layer is inhibited.

2. A disposable diaper as claimed in claim 1 in which said upper ply and said lower ply are disposed in spaced-apart, substantially parallel relationship on opposite sides of a layer of particles of water-absorbing polymer.

3. A disposable diaper as claimed in claim 1, in which said high wet strength paper is paper treated so as to have a minimum wet strength of at least 55 grams per one inch.

4. A disposable diaper as claimed in claim 1, in which said low wet strength paper is crepe paper or tissue paper not treated to increase its wet strength.

* * * * *

UNITED STATES PATENT AND TRADEMARK OFFICE
CERTIFICATE OF CORRECTION

PATENT NO. : 4 269 188

DATED : May 26, 1981

INVENTOR(S) : Kazunori Nishizawa et al

It is certified that error appears in the above—identified patent and that said Letters Patent is hereby corrected as shown below:

Column 4, Line 66; change "claim 1" to ---claim 1 or claim 3---.

Signed and Sealed this

Twenty-fifth Day of August 1981

[SEAL]

Attest:

Attesting Officer

GERALD J. MOSSINGHOFF

Commissioner of Patents and Trademarks